United States Patent [19]

Bronder

[11] Patent Number: 5,922,360
[45] Date of Patent: Jul. 13, 1999

[54] STABILIZED ORTHOSILICIC ACID COMPRISING PREPARATION AND BIOLOGICAL PREPARATION

[75] Inventor: Stefan Raymond Bronder, Aalst, Belgium

[73] Assignee: Bio Pharma Sciences B.V., Netherlands

[21] Appl. No.: 08/687,381

[22] PCT Filed: Feb. 7, 1995

[86] PCT No.: PCT/NL95/00054

§ 371 Date: Jan. 22, 1997

§ 102(e) Date: Jan. 22, 1997

[87] PCT Pub. No.: WO95/21124

PCT Pub. Date: Aug. 10, 1995

[30] Foreign Application Priority Data

Feb. 7, 1994 [NL] Netherlands .......................... 94.00189

[51] Int. Cl.$^6$ ........................ A61K 31/695; A61K 33/00; A01N 55/10
[52] U.S. Cl. ........................... 424/600; 424/724; 514/63; 514/970
[58] Field of Search .................................... 424/600, 724; 514/63, 970

[56] References Cited

U.S. PATENT DOCUMENTS 4,466,958 8/1984 Morrison ................................. 424/724
4,487,712 12/1984 Wilson et al. ......................... 252/78.3

FOREIGN PATENT DOCUMENTS 373110 4/1923 Germany .

OTHER PUBLICATIONS

'Gmelins Handbuch der Anorganischen Chemie Silicium Part B', 1959 Verlag Chemie GmbH.

P. Pascal 'Nouveau Traite de Chimie Minerale Paul Pascal Part VIII 2nd volume Silicium', 1965, Masson and CY, Paris, FR.

Holleman–Wiberg 'Lehrbuch der Anorganischen Chemie', 1976, Verlag de Gruyter, Berlin, DE.

Primary Examiner—John Pak
Attorney, Agent, or Firm—Webb Ziesenheim Logsdon Orkin & Hanson, P.C.

[57] ABSTRACT

A preparation comprising ortho silicic acid which is stabilized with a stabilizing agent and is substantially free of organic silicon compounds, preferably a nitrogen-containing stabilizing agent such as choline, to a method for preparing such a preparation, comprising: i) providing a solution containing a stabilizing agent; ii) dissolving an inorganic silicon compound in the solution containing the stabilizing agent; and iii) hydrolyzing the silicon compound to ortho silicic acid, and to the obtained biological preparation.

14 Claims, No Drawings

STABILIZED ORTHOSILICIC ACID COMPRISING PREPARATION AND BIOLOGICAL PREPARATION

This application is a 371 of PCT/NL95/00054, filed on Feb. 7, 1995.

Silicon is an essential trace element for plants, animals and humans. In a watery environment silicon is initially present as ortho silicic acid which is quickly converted by polycondensation to polysilicic acid, which transposes into a colloidal solution and gels. Ultimately, insoluble silicates are formed.

In the same way as carbonic acid for compounds comprising carbon, ortho silicic acid is the most important metabolite for organic silicon compounds. Water glass (sodium ortho silicate) is the usual source of ortho silicic acid, which however hydrolyses after oral administration to mammals and forms insoluble and non-absorbable gels through polycondensation.

Organic silicon compounds such as alcohol esters, such as ethyl ortho silicate and glycol ortho silicate, cannot be used in biological systems because of the poor solubility and the low resistance to hydrolysis, but above all because of the unacceptable toxicity.

There therefore exists a need for a silicon-comprising preparation not possessing the above stated drawbacks, because silicon has a positive biological effect on nails, hair, skin, teeth, collagen, connective tissue, bones, encourages cell generation, stimulates the immune system against infections and toxins and inhibits degenerative (ageing)-processes.

The present invention is based on the insight that if ortho silicic acid is formed in the presence of a stabilizing agent, polycondensation is inhibited and even avoided and, furthermore organic silicon compounds substantially do not occur.

A first aspect of the present invention therefore relates to a preparation comprising ortho silicic acid which is stabilized with a stabilizing agent and is substantially free of organic silicon compounds.

A second aspect of the present invention relates to a method for preparing a preparation as according to claims 1–7, which comprises of:

i) providing a solution containing a stabilizing agent;
ii) dissolving an inorganic silicon compound in the solution containing the stabilizing agent; and
iii) hydrolyzing the silicon compound to ortho silicic acid.

A third aspect of the present invention relates to a biological preparation containing a preparation according to claims 1–7, and/or a preparation prepared according to claims 8–13, and a pharmacologically acceptable diluent.

The biological preparation according to the invention can be used for:

chronic infections with destruction of the mucous membranes: forms of sinusitis and ulcers.

problems with connective tissues, arteriosclerosis, bone and tendon problems, gynaecology (fibroids, polycystic adenopathy); and the growth of children: children with recurrent infections with overload of the lymphatic system.

The stabilization using a stabilizing agent preferably takes place with stabilizing agents containing a nitrogen atom with a free electron pair which forms a complex with the silanol groups of the ortho silicic acid. Quaternary ammonium compounds are preferably used, for instance tetra-alkyl compounds, wherein each alkyl group contains for instance 1–5 carbon atoms, in particular methyl and ethyl groups. Very highly recommended are trialkylhydroxyalkyl compounds, wherein the hydroxy group is preferably methanol or ethanol. Choline has been found very suitable, which is further recommended in that it provides the option of the stabilizing agent also forming the solution for the ortho silicic acid, and an inert solvent can therefore be omitted.

Another or additional type of stabilizing agent is an amino acid, such as proline and serine. Serine enhances uptake in the stomach and gives additional stability.

Starting point for the preparation of the ortho silicic acid-comprising preparation is a solution containing the stabilizing agent, wherein an inert solvent can be used. Incorporated in -This solution is an inorganic silicon compound which hydrolysis under the influence of water to ortho silicic acid, which is immediately stabilized by the stabilizing agent that is present. The solution containing the stabilizing agent can initiate the hydrolysis immediately after addition of the inorganic silicon compound. Usually recommended is a solution containing a stabilizing agent in which no hydrolysis can take place until after the addition of a hydrolyzing agent, such as water.

If choline is used as stabilizing agent it can be converted to choline hydrochloride using dry hydrochloric acid. In this liquid stabilizing agent can be incorporated the inorganic silicon compound, such as a silicon halogenide, particularly silicon tetrachloride.

Simultaneously with the addition of the inorganic silicon compound, or following the addition of the hydrolyzing agent, the hydrolysis of the inorganic silicon compound to ortho silicic acid takes place. The silicic acid formed in situ is subsequently stabilized by forming a complex with the stabilizing agent. It is of great importance herein that the stabilizing agent only forms a complex and does not enter into a reaction, particularly an esterifying reaction, with the ortho silicic acid. Then achieved is that no organic silicon compounds are created which have an inherent toxicity, are absorbed in the stomach and enter the blood circulation.

After forming a complex the ortho silicic acid-comprising solution can if desired be partially neutralized by adding a base, such as a lye, particularly sodium hydroxide. Neutralization can take place to a pH smaller than 4, in particular smaller than 3, in general to a pH lying in the range of 1–3, whereby any polycondensation of ortho silicic acid is substantially avoided.

If desired, a further purification of the preparation can take place, for instance through absorption of contaminants on active carbon, optionally followed by filtration.

If desired, the content of hydrolyzing agent, particularly water, can be reduced by removing the hydrolyzing agent, for instance through distillation, whereby a constant viscosity is achieved if use is made of choline as the stabilizer.

Preparations then result with a silicon content generally of 1% by weight, preferably of about 4% by weight, such as 8% by weight. A very acceptable preparation contains 3–5% by weight of silicon, 70s by weight of choline hydrochloride and the rest water. The pH of this preparation lies within the range 1–3.

Biological preparations can be-manufactured from this prepared preparation for the purpose of administering ortho silicic acid to plants, animals and humans, whereby the bio-availability of silicon is greatly improved. The above prepared solution can be administered as biological preparation as such, for instance as nail tincture. A usage of 0.5 ml of a 2% Si-solution per day for three weeks caused a fungal infection to disappear (3 patients), where treatment with ketonazols did not render any improvement. If for instance an edible acid, such as malic acid, is added a preparation results which is very suitable for administering to horses.

If a solid carrier is added, for instance cattle feed, cattle feed pellets can be pressed therefrom which contain ortho silicic acid in stabilized form for administering silicon to cattle. If sugar/maltose is used as solid carrier, tablets and gels can be formed therefrom.

Through use of a glucuronic acid buffer a preparation on a cream basis can be formed wherein the pH is less than 4, which creams are suitable for local cutaneous application.

It will be apparent that all kinds of diluents can be used in order to obtain a preparation for biological application. Such diluents contain lower alkanols, such as ethanol, dichloromethane, ethyl acetate, glycerine and polyalcohols.

PREPARATION EXAMPLE

Choline hydrochloride (UCB) is dried under vacuum (100° C./6 hours). The choline hydrochloride is treated with dry hydrochloric acid. Silicon hydrochloride (1 mol per mol) is added to the formed choline solution at a temperature which is kept below 40° C.

For hydrolysis, water (ice/ice water) is added to the solution while cooling, wherein the temperature is held within the range of −20° C. to −30° C.

The solution containing the ortho silicic acid is subsequently neutralized by adding sodium hydroxide wherein cooling takes place to a temperature below 0° C. The pH neutralization amounts to about 1.3.

A purification over active carbon is then performed, followed by filtering off the formed precipitate and the active carbon.

After distillation under vacuum a preparation is obtained which contains 3% by weight of silicon, 70% by weight choline hydrochloride and the rest water.

FAB/MS with glycerol as liquid matrix provides a spectrum with a molecular cation at M/Z 104 ($C^+$) and an $MC^+$ adduction at M/Z243/245, typical for chloride isotropy. This spectrum is the same as the spectrum for choline.

NMR-SPECTRUM OF THE PREPARATION SHOWING CHOLINE/ALCOHOL GROUPS

Element analysis produces 24±2% by weight chlorine and 9±1% by weight N. This points to a ratio of chloride to nitrogen of 1:1.

Neutralization is subsequently carried out to a pH of 2.7–3.0.

The preparation is stable for more than two years when stored at room temperature.

FORMULATION EXAMPLES

Formulation Example A

The biological preparation contains 3% by weight silicon in the form of ortho silicic acid, 70% by weight choline hydrochloride, the rest water and a pH of 2.7–3.0. This liquid is suitable for oral and cutaneous administering.

Formulation Example B

The biological preparation as prepared above is mixed with cattle feed which ultimately contains silicon as ortho silicic acid in a concentration of 0.001–0.005% by weight. This mixture can be pressed to pellets which are administered to cattle.

Formulation Example C

The preparation A is mixed with sugar and/or maltose which is pressed to tablets containing silicon in the form of ortho silicic acid at a content of 0.1–0.2% Si by weight.

Formulation Example D

A silicon-comprising cream is prepared as follows. A fat phase containing Imwitor 960 (Hüls) 7%, Miglyol 812 10%, Softigon 701 (Hüls) 2%, Marlowet TA 25 (Hüls) 2%, Lanette N (Henkel) 4%, Isopropylmyristate 3%, a water phase containing Inositol 0.2%, Gluconate buffer 0.05 M, pH 3.8 ad 100, Glycerol 10% and the preparation A, as well as a perfume.

The fat phase is melted at 80° C., whereafter the water phase, also heated to 80° C., is admixed, followed by cooling. Shortly before solidifying, the preparation A and perfume (4 drops) are added. The cream eventually contains 0.01–0.05% by weight silicon as ortho silicic acid.

Flavourings can be added if desired, for instance by dilution (1:30) in a 0.01 M citrate buffer (pH 3.5–3.8) and by adding a flavouring (raspberry and the like).

I claim:

1. Preparation comprising ortho silicic acid which is stabilized with at least one silicic acid stabilizing agent containing nitrogen, said at least one silicic acid stabilizing agent further being selected from the group consisting of a quaternary ammonium stabilizer and an amino acid stabilizer, said composition being substantially free of organic silicon compounds and further being characterized in that when the stabilized ortho silicic acid is in aqueous solution polycondensation of ortho silicic acid is substantially avoided.

2. Preparation as claimed in claim 1, wherein the quaternary ammonium compound is a tetra-alkyl ammonium compound.

3. Preparation as claimed in claim 2, wherein the quaternary ammonium compound is a trialkylhydroxyalkyl ammonium compound.

4. Preparation as claimed in claim 3, wherein the quaternary ammonium compound is a choline.

5. Biological preparation containing a preparation as claimed in claim 1 in combination with a pharmacologically acceptable diluent.

6. The composition according to claim 1, further containing a diluent selected from the group consisting of alkanols and dichloromethane.

7. The composition according to claim 1, further containing a polyalchol diluent.

8. The composition according to claim 7, wherein said polyalcohol is selected from the group consisting of glycerol and inositol.

9. Method for stabilizing an ortho silicic acid with a stabilizing agent and thereby preparing a preparation as claimed in claim 1, which comprises of:

i) providing a solution containing a silicic acid stabilizing agent containing nitrogen selected from the group consisting of quaternary ammonium stabilizer and an amino acid stabilizer;

ii) dissolving an inorganic silicon compound, which is capable of capable of forming ortho silicic acid, in the solution containing the stabilizing agent; and iii) hydrolyzing the silicon compound to ortho silicic acid.

10. Method as claimed in claim 9, wherein the silicon compound is a silicon halogenide.

11. Method as claimed in claim 10, wherein the silicon compound is silicon tetrachloride.

12. Method as claimed in claim 11, wherein the solution containing the stabilized ortho silicic acid is brought to a pH lower than 4.

13. Method as claimed in claim 12, wherein the stabilizing agent is a chloride of said stabilizing agent.

14. Method as claimed in claim 13, wherein the solution containing the stabilized ortho silicic acid is concentrated to a silicon content greater than 1% by weight.

* * * * *

UNITED STATES PATENT AND TRADEMARK OFFICE
CERTIFICATE OF CORRECTION

PATENT NO. : 5,922,360
DATED : July 13, 1999
INVENTOR(S) : Stefan Raymond Bronder It is certified that error appears in the above-identified patent and that said Letters Patent is hereby corrected as shown below:

Column 1 Line 50 after "invention" delete --is--.

Column 2 Line 10 "Incorporated in -This" should read --Incorporated in this--.

Column 2 Line 50 "70s" should read --70%--.

Column 2 Line 53 "be-manufactured" should read --be manufactured--.

Signed and Sealed this

First Day of February, 2000

Attest:

Q. TODD DICKINSON

*Attesting Officer*    *Acting Commissioner of Patents and Trademarks*

UNITED STATES PATENT AND TRADEMARK OFFICE
CERTIFICATE OF CORRECTION

PATENT NO. : 5,922,360
DATED      : July 13, 1999
INVENTOR(S): Stefan Raymond Bronder It is certified that error appears in the above-identified patent and that said Letters Patent is hereby corrected as shown below:   In the Claims:

In claim 6, Column 4 Lines 35-37, after "containing a" delete "diluent selected from the group consisting of alkanols and dichloromethane" and insert --polyalcohol diluent--.

In claim 7, Column 4 Lines 38-39, after "containing a" delete "polyalcohol diluent" and insert --diluent selected from the group consisting of glycerine and polyalcohol--.

In claim 9, paragraph (ii), Column 4, line 50, "capable of capable of" should read -- capable of --.

Signed and Sealed this

Twenty-eighth Day of March, 2000

Attest:

Q. TODD DICKINSON

Attesting Officer

Commissioner of Patents and Trademarks